United States Patent [19]

Regnier et al.

[11] 4,112,092
[45] Sep. 5, 1978

[54] 1-NAPHTHYLMETHYL-4-(THIAZOLYL-2)-PIPERAZINES

[75] Inventors: Gilbert Regnier, Chatenay-Malabry; Roger Canevari, Elancourt; Jean-Claude Poignant, Bures, Yvette, all of France

[73] Assignee: Science Union et Cie, France

[21] Appl. No.: 785,855

[22] Filed: Apr. 8, 1977

[30] Foreign Application Priority Data

Apr. 12, 1976 [GB] United Kingdom ............... 14811/76

[51] Int. Cl.² .................. C07D 417/04; A61K 31/495
[52] U.S. Cl. .................................... 424/250; 544/367; 544/403
[58] Field of Search ................... 260/268 H, 268 BC; 424/250

[56] References Cited
U.S. PATENT DOCUMENTS 3,941,789  3/1976  Renth et al. ................... 260/268 BC
3,944,551  3/1976  Regnier et al. ................ 260/268 BC Primary Examiner—Jose Tovar
Attorney, Agent, or Firm—Gordon W. Hueschen

[57] ABSTRACT

Naphthyl derivatives of the formula:

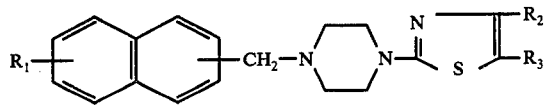

wherein:
R₁ is hydrogen, halogen, lower alkyl or lower alkoxy, and
R₂ and R₃, which are the same or different, are hydrogen, lower alkyl or phenyl,
or R₂ and R₃ joined together are —CH=CH—CH=CH—.

These compounds are used as medicines, especially in the treatment of disorders of central nervous system (CNS), Parkinson's disease and cardiovascular disorders.

6 Claims, No Drawings

1-NAPHTHYLMETHYL-4-(THIAZOLYL-2)-PIPERAZINES

The present invention provides naphthyl derivatives of the formula I:

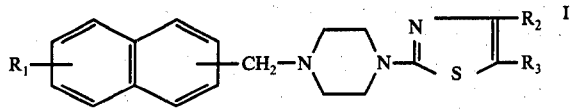

and acid addition salts, especially physiologically tolerable acid addition salts thereof, wherein:

$R_1$ is selected from the group consisting of a hydrogen atom, halogen atoms, alkyl and alkoxy radicals each having from 1 to 5 carbon atoms inclusive, and $R_2$ and $R_3$, which are the same or different, are selected from the group consisting of a hydrogen atom, alkyl radicals having from 1 to 5 carbon atoms inclusive, and a phenyl radical, and $R_2$ and $R_3$ joined together are a $-CH=CH-CH=CH-$ radical, in order to form with the thiazolyl radical to which they are bonded a benzothiazolyl radical.

The halogen atoms mentioned in the meaning of $R_1$ may be, for example, chlorine, fluorine or bromine atoms.

The alkyl radical mentioned in the meaning of $R_1$, $R_2$ and $R_3$ may be, for example, methyl, ethyl, propyl, butyl or pentyl radicals, and the alkoxy radicals given in the meaning of $R_1$, may be, for example, methoxy, ethoxy, propoxy, butoxy and pentyloxy radicals.

The compounds of the general formula I are new, and they were prepared according to the following methods which are all included in the present invention.

The present invention provides a process for preparing a compound of the general formula I which comprises either (a) condensing a compound of the general formula II:

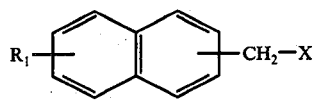

in which $R_1$ has the meaning given above and X is a chlorine or a bromine atom, with a N-monosubstituted piperazine of the general formula III:

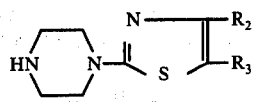

in which $R_2$ and $R_3$ have the meanings given above; or (b) condensing a compound of the general formula IV:

in which $R_2$, $R_3$ and X have the meanings given above, with a N-monosubstituted piperazine of the general formula V:

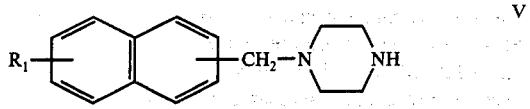

in which $R_1$ has the meaning given above.

The above condensations are advantageously carried out in solution in a polar solvent, for example an alcohol such as butanol or iso-amyl alcohol, or an aliphatic amide, such as dimethyl formamide, or in a non-polar solvent for example an aromatic hydrocarbon, such as xylene. It is advantageous to carry out the processes at a temperature of from 115° to 160° C. in the presence of an acceptor for the hydrogen halide formed during the reaction, for example, an alkali metal salt of carbonic acid, such as sodium or potassium carbonate, or an organic base such as triethylamine; if desired, there may be used an excess of the N-monosubstituted piperazine of the formula III or V, the excess acting as an acceptor.

The present invention also provides a process for preparing a compound of the general formula I which comprises submitting a mixture of an aldehyde of the general formula VI:

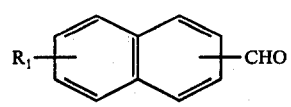

in which $R_1$ has the meaning given above, and a N-monosubstituted piperazine of the general formula III given above, to alkylating reduction with hydrogen at a pressure $\leq$ 5 atmospheres, preferably at a pressure of from 2 to 5 atmospheres, in the presence of a small quantity of palladium-on-charcoal as catalyst, in a suitable solvent, such as an alcohol having up to five carbon atoms or ethyl acetate.

Such a process is advantageously carried out by submitting to hydrogenation under a hydrogen pressure of from 2 to 5 atmospheres, a substantially equimolecular mixture of the compounds of the formulae III and VI, in solution in ethyl acetate, in the presence of palladium-on-charcoal as catalyst at a temperature of from 60° to 80° C.

The starting materials used for these processes are known compounds or they are prepared according to methods described in the literature for preparing similar compounds.

The compounds of the general formula I are weak bases which may be converted by treatment with acids into acid addition salts. As acids which may be used for the formation of these addition salts, there may be mentioned for example, in the mineral series: hydrochloric, hydrobromic, sulfuric and phosphoric acids, and in the organic series: acetic, propionic, maleic, fumaric, tartaric, citric, oxalic, benzoic, methanesulphonic and isethionic acids.

The compounds of the formula I may be purified by physical methods, for example, by distillation, crystallization or chromatography, or by chemical methods, for example by formation of an addition salt followed by crystallization of the latter and decomposition thereof with an alkaline agent.

The compounds of the general formula I and physiologically tolerable acid addition salts thereof possess valuable pharmacological and therapeutic properties, especially central nervous system stimulating, anti-Parkinson and cardiovascular properties. They may, therefore, be used as medicines, especially in the treatment of disorders of central nervous system (CNS), Parkinson's disease and cardiovascular disorders.

Their toxicity is low and their $LD_{50}$ determined in mice by intraperitoneal route is higher than 200 mg/kg.

Their neuroleptic properties were evidenced in the rats and mice by modifications observed on the stereotypy, motility and excitation.

In mice, the average effective dose is about 50 mg/kg by intraperitoneal route. At this dose, there were observed a decrease of motility and tonus.

The scores of CNS stimulation or stereotypy were determined according to the method of Quinton and Haliwell, Nature 200 N° 4902, p. 178 (1963). Scores of up to 266 for 3 hours were observed with a dose of 80 mg/kg I.P.

The present invention also provides pharmaceutical compositions which contains a compound of the general formula I or a physiologically tolerable salt thereof in admixture or conjunction with a pharmaceutically suitable carrier, such for example, as distilled water, glucose, lactose, starch, talc, magnesium stearate, ethyl cellulose or cocoa butter.

The so-obtained pharmaceutical compositions are advantageously in unit dosage form and may contain from 15 to 150 mg of the active ingredient.

These pharmaceutical compositions may be in form of tablets, dragees, capsules, suppositories or injectable or drinkable solutions and may be administered by oral, rectal or parenteral route at a dose of 15 to 150 mg, 1 to 5 times a day.

The following examples illustrate the invention, the melting points being determined in a capillary tube.

EXAMPLE 1

1-(2-naphthylmethyl)-4-(2-thiazolyl)-piperazine

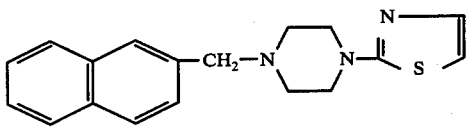

First method

To a solution of 22.1 g (0.1 mole) of 2-bromomethyl-naphthalene in 150 ml of dimethylformamide, there were added successively 10.7 g (0.101 mole) of dry potassium carbonate and 17.2 g (0.101 mole) of 1-(2-thiazolyl)-piperazine. The resulting suspension was heated at 150° C. for 10 hours; the salt which had formed was then filtered off and the dimethylformamide was evaporated off under reduced pressure. There was obtained a brown crystalline residue which was washed with water and suction filtered off. The resulting 29 g of crystals were recrystallized in 150 ml of ethanol to give 20 g of 1-(2-naphthylmethyl)-4-(2-thiazolyl)-piperazine as beige crystals melting at 83°–84° C.

Second method

In a manner similar to that described above, but starting from 45.2 g (0.2 mole) of 1-(2-naphthylmethyl)-piperazine and 12 g (0.1 mole) of 2-chlorothiazole in 150 ml of dimethylformamide at 150° C., there were obtained 17 g of 1-(2-naphthylmethyl)-4-(2-thiazolyl)-piperazine as beige crystals melting at 83°–84° C.

Third method

A solution of 15.6 g (0.1 mole) of β-naphthaldehyde and 16.9 g (0.1 mole) of 1-(2-thiazolyl)-piperazine in 150 ml of ethyl acetate was hydrogenated under a hydrogen pressure of 5 atmospheres, in the presence of 2 to 5 g of palladium-on-charcoal containing 10% of palladium, at a temperature of 50° C. After the absorption of the theoretical amount of hydrogen, the catalyst was filtered off and the solvent was evaporated off under reduced pressure.

There were obtained 28 g of a crystalline residue, which recrystallized in 150 ml of ethanol, gave 18 g of 1-(2-naphthylmethyl)-4-(2-thiazolyl)-piperazine as beige crystals melting at 83°–84° C.

EXAMPLES 2 to 11

The following compounds were prepared according to the methods described in Example 1.

2. 1-(2-naphthylmethyl)-4-(4-methyl-2-thiazolyl)-piperazine, M.P. 75°–76° C. (anhydrous ethanol), starting from:

2-bromomethylnaphthalene and 1-(4-methyl-2-thiazolyl)-piperazine, or 1-(2-naphthylmethyl)-piperazine and 4-methyl-2-chlorothiazole, or β-naphthaldehyde and 1-(4-methyl-2-thiazolyl)-piperazine.

3. 1-(2-naphthylmethyl)-4-(4-phenyl-2-thiazolyL)-piperazine, starting from:

2-bromomethylnaphthalene and 1-(4-phenyl-2-thiazolyl)-piperazine, or 1-(2-naphthylmethyl)-piperazine and 4-phenyl-2-chloro-thiazole, or β-naphthaldehyde and 1-(4-phenyl-2-thiazoly)-piperazine.

4. 1-(2-naphthylmethyl)-4-(4,5-dimethyl-2-thiazolyl)-piperazine, starting from:

2-bromomethylnaphthalene and 1-(4,5-dimethyl-2-thiazolyl)-piperazine, or 1-(2-naphthylmethyl)-piperazine and 4,5-dimethyl-2-chlorothiazole, or β-naphthaldehyde and 1-(4,5-dimethyl-2-thiazolyl)-piperazine.

5. 1-(2-naphthylmethyl)-4-(2-benzothiazolyl)-piperazine, starting from:

2-bromomethylnaphthalene and 1-(2-benzothiazolyl)-piperazine, or 1-(2-naphthylmethyl)-piperazine and 2-chlorobenzothiazole, or β-naphthaldehyde and 1-(2-benzothiazolyl)-piperazine.

6. 1-(6-chloro-2-naphthylmethyl)-4-(2-thiazolyl)-piperazine, M.P. 134°–135° C. (ethanol), starting from:

6-chloro-2-chloromethylnaphthalene and 1-(2-thiazolyl)-piperazine, or 1-(6-chloro-2-naphthylmethyl)-piperazine and 2-chlorothiazole, or 6-chloro-β-naphthaldehyde and 1-(2-thiazolyl)-piperazine.

7. 1-(6-methyl-2-naphthylmethyl)-4-(2-thiazolyl)-piperazine, M.P. 104°–106° C. (ethanol at 80%), starting from:

6-methyl-2-bromomethylnaphthalene and 1-(2-thiazolyl)-piperazine, or 1-(6-methyl-2-naphthylmethyl)-piperazine and 2-chlorothiazole, or 6-methyl-β-naphthaldehyde and 1-(2-thiazolyl)-piperazine.

8. 1-(6-methoxy-2-naphthylmethyl)-4-(2-thiazolyl)-piperazine, M.P. 146°–148° C. (anhydrous ethanol), starting from:

6-methoxy-2-bromomethylnaphthalene and 1-(2-thiazolyl)-piperazine, or 1(6-methoxy-2-naphthylmethyl)-piperazine and 2-chlorothiazole, or 6-methoxy-β-naphthaldehyde and 1-(2-thiazolyl)-piperazine.

9. 1-(7-chloro-1-naphthylmethyl)-4-(2-thiazolyl)-piperazine, M.P. 139°–140° C. (ethanol), starting from:

7-chloro-1-chloromethylnaphthalene and 1-(2-thiazolyl)-piperazine, or 1-(7-chloro-1-naphthylmethyl)-piperazine and 2-chlorothiazole, or 7-chloro-α-naphthaldehyde and 1-(2-thiazolyl)-piperazine.

10. 1-(7-methyl-1-naphthylmethyl)-4-(2-thiazolyl)-piperazine, M.P. 101°–103° C. (ethanol at 80%), starting from:

7-methyl-1-chloromethyl naphthalene and 1-(2-thiazolyl)-piperazine, or 1-(7-methyl-1-naphthylmethyl)-piperazine and 2-chlorothiazole, or 7-methyl-α-naphthaldehyde and 1-(2-thiazolyl)-piperazine.

11. 1-(1-naphthylmethyl)-4-(2-thiazolyl)-piperazine, starting from:

1-bromomethylnaphthalene and 1-(2-thiazolyl)-piperazine, or 1-(1-naphthylmethyl)-piperazine and 2-chlorothiazole, or α-naphthaldehyde and 1-(2-thiazolyl)-piperazine.

The following examples illustrate the pharmaceutical compositions containing as active ingredient, a compound of the general formula I:

EXAMPLE 12

Formulation for one capsule containing 100 mg of active ingredient:

| | | |
|---|---|---|
| 1-(2-naphthylmethyl)-4-(2-thiazolyl)-piperazine | 100 | mg |
| microcristalline cellulose | 75 | mg |
| colloidal silica | 0.3 | mg |
| polyvinylpolypyrrolidone | 5 | mg |
| capsule No. 2 | 1 | |

EXAMPLE 13

Formulation for one ampul containing 20 mg of 1-(2-naphthylmethyl)-4-(2-thiazolyl)-piperazine.

| | | |
|---|---|---|
| 1-(2-naphthylmethyl)-4-(2-thiazolyl)-piperazine bis methane sulfonate | 32.5 | mg |
| sodium chloride | 40 | mg |
| water for injectable solution (by intravenous route) q.s. for | 5 | ml. |

We claim:
1. A compound selected from the group consisting of:
(A) naphthyl compounds of the formula I:

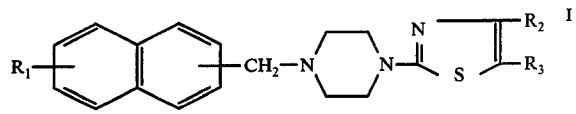

wherein:
$R_1$ is selected from the group consisting of hydrogen, halogen, i.e. chlorine, fluorine, or bromine, lower-alkyl and lower-alkoxy, each having 1 to 5 carbon atoms inclusive, $R_2$ and $R_3$, which are the same or different, are selected from the group consisting of hydrogen, lower-alkyl having 1 to 5 carbon atoms inclusive and phenyl and $R_2$ and $R_3$ joined together are —CH=CH—CH=CH— in order to form with the thiazolyl radical to which they are bonded a benzothiazolyl radical; and (B) physiologically tolerable acid addition salts thereof.

2. A compound of claim 1 which is 1-(2-naphthylmethyl)-4-(2-thiazolyl)-piperazine.

3. A compound of claim 1 which is 1-(1-naphthylmethyl)-4-(2-thiazolyl)-piperazine.

4. A compound of claim 1 which is 1-(7-methyl-1-naphthylmethyl)-4-(2thiazolyl)-piperazine.

5. A pharmaceutical composition useful for treating CNS disorders containing as active ingredient a compound of claim 1 in an amount of 15 to 150 mg, together with a suitable pharmaceutical carrier.

6. A method for treating a living animal body afflicted with a disorder of the central nervous system, comprising the step of administering a compound of claim 1 in an amount effective for the alleviation of the said condition.

* * * * *